United States Patent
Lindner et al.

(10) Patent No.: US 9,586,015 B1
(45) Date of Patent: Mar. 7, 2017

(54) DUTY-CYCLE INDICATOR FOR MANUAL RESUSCITATION/VENTILATION

(71) Applicants: Chance S. Lindner, Scottsdale, AZ (US); Mary E. Lindner, Baxter, MN (US)

(72) Inventors: Chance S. Lindner, Scottsdale, AZ (US); Mary E. Lindner, Baxter, MN (US)

(73) Assignee: Chance S. Lindner, Scottsdale, AZ (US)

( * ) Notice: Subject to any disclaimer, the term of this patent is extended or adjusted under 35 U.S.C. 154(b) by 0 days.

(21) Appl. No.: 14/226,634

(22) Filed: Mar. 26, 2014

Related U.S. Application Data

(60) Provisional application No. 61/879,044, filed on Sep. 17, 2013.

(51) Int. Cl.
*A61M 16/00* (2006.01)
*G09B 23/28* (2006.01)

(52) U.S. Cl.
CPC ....... *A61M 16/0051* (2013.01); *G09B 23/288* (2013.01)

(58) Field of Classification Search
CPC ...... A61M 2016/0084; A61M 16/0078; A61M 16/0051; A61M 16/00; G09B 23/288
USPC ............ 128/205.13, 202.22, 207.12, 204.23, 128/205.23, 204.18
See application file for complete search history.

(56) References Cited

U.S. PATENT DOCUMENTS

| | | | | |
|---|---|---|---|---|
| 5,211,170 | A * | 5/1993 | Press | A61M 16/00 128/204.18 |
| 5,772,394 | A | 6/1998 | Yokota et al. | 415/56.1 |
| 7,051,596 | B1 | 5/2006 | Lau et al. | 73/716 |
| 7,172,557 | B1 | 2/2007 | Parker | 600/529 |
| 7,357,033 | B2 | 4/2008 | Lau et al. | 73/736 |
| 2003/0192547 | A1 * | 10/2003 | Lurie | A61H 31/005 128/207.12 |
| 2006/0060199 | A1 * | 3/2006 | Lampotang | A61M 16/0078 128/205.13 |
| 2007/0049976 | A1 * | 3/2007 | Ni | G09B 23/288 607/9 |
| 2008/0053445 | A1 * | 3/2008 | Kroupa et al. | 128/205.23 |
| 2012/0302910 | A1 * | 11/2012 | Freeman et al. | 600/538 |
| 2014/0154792 | A1 * | 6/2014 | Moynihan et al. | 435/287.2 |
| 2014/0275820 | A1 * | 9/2014 | Varga | A61M 16/0078 600/301 |
| 2015/0283342 | A1 * | 10/2015 | Mielcarz | G09B 23/288 128/202.22 |

* cited by examiner

*Primary Examiner* — Peter S. Vasat
*Assistant Examiner* — Mark Wardas
(74) *Attorney, Agent, or Firm* — Hayes Soloway P.C.

(57) ABSTRACT

A pacing apparatus for use with a manual ventilation device, includes electronic circuitry configured to provide a visual, tactile and/or audible indication of a specified compression/ventilation duty-cycle for delivering compressions/ventilations in order to ventilate, provide air, oxygen or other medical gas to a patient or training device.

19 Claims, 4 Drawing Sheets

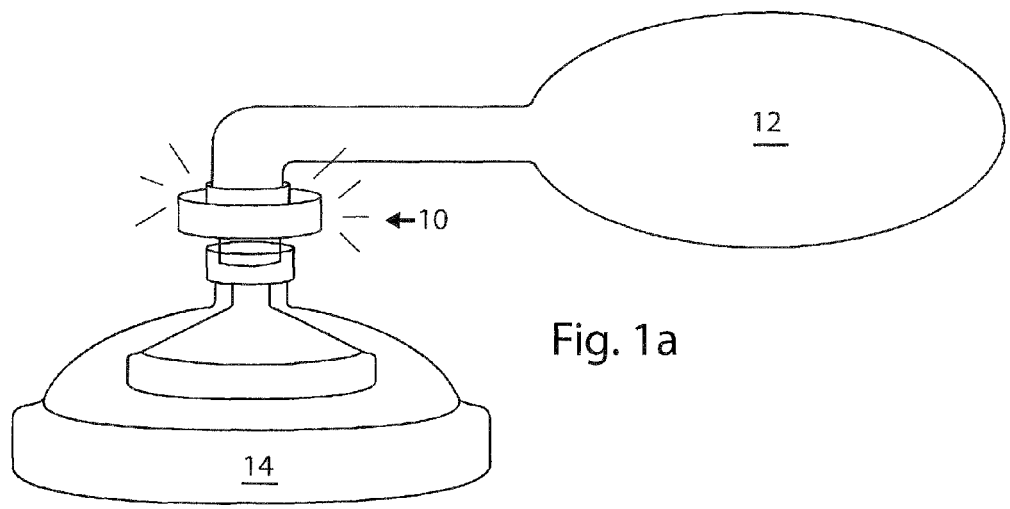
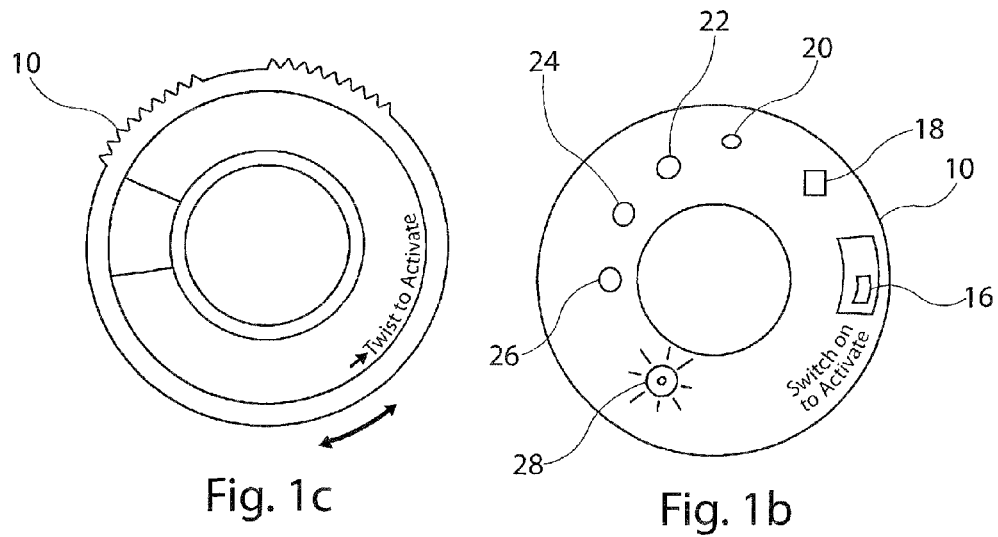
Fig. 1a
Fig. 1c
Fig. 1b

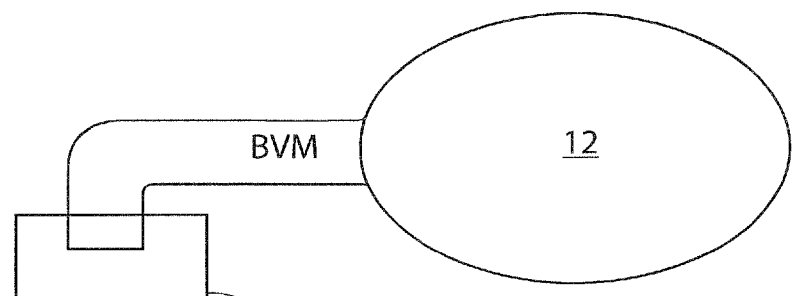
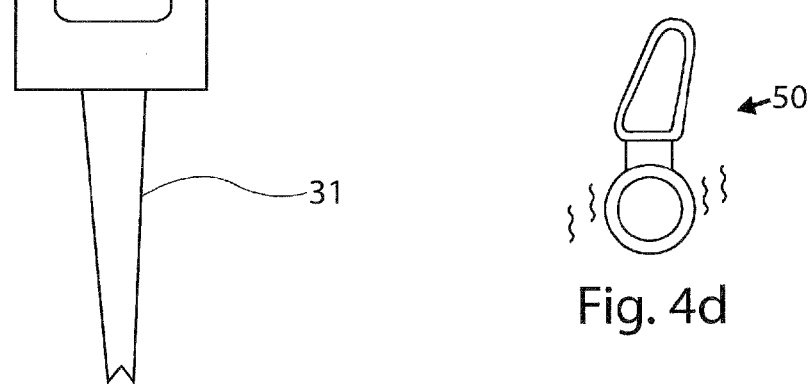
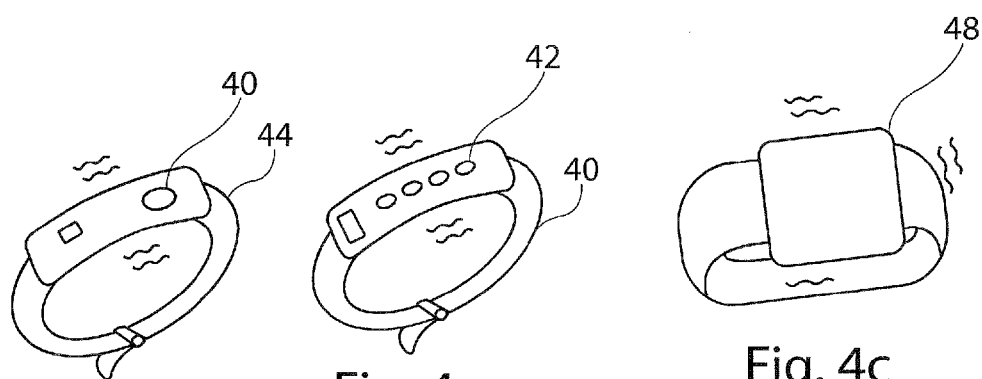
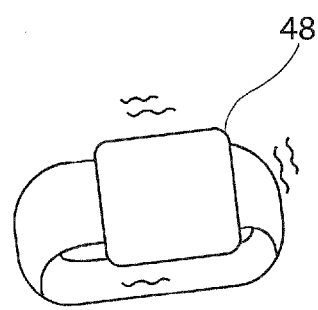

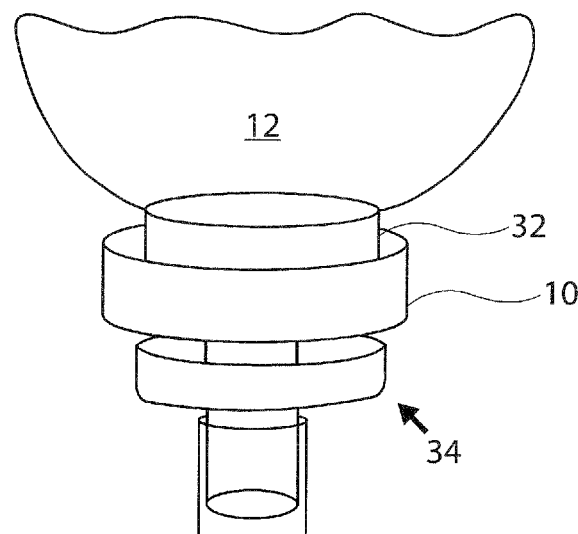
Fig. 3a
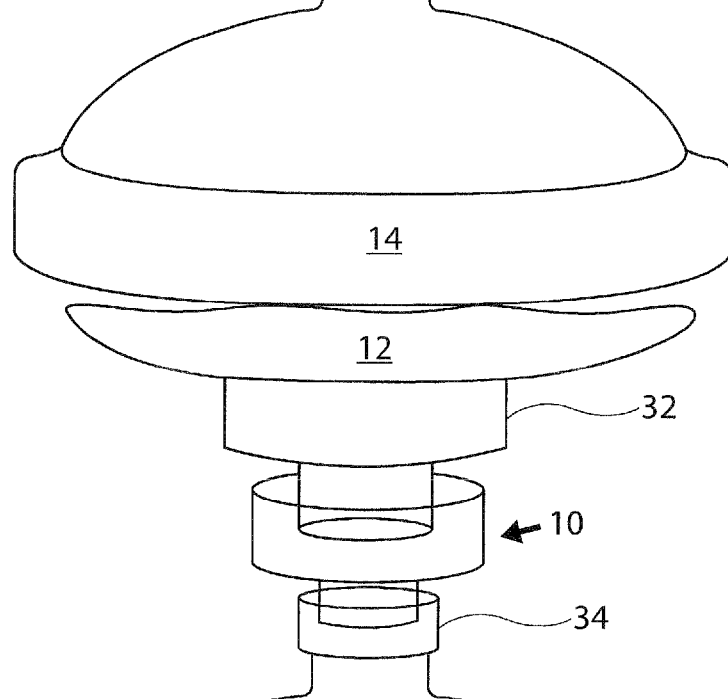
Fig. 3b
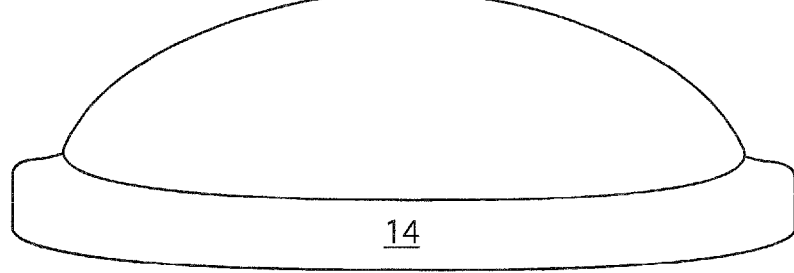

DUTY-CYCLE INDICATOR FOR MANUAL RESUSCITATION/VENTILATION

CROSS REFERENCE TO RELATED APPLICATION

This application claims priority from U.S. Provisional Application Ser. No. 61/879,044, filed Sep. 17, 2013.

FIELD OF THE INVENTION

This invention pertains to devices and methods for applying manual ventilation assistance to patients as well as training aids and the timing/duration of the ventilations.

BACKGROUND

A manual resuscitator/ventilator is a hand-held device used to provide positive pressure ventilation to patients who are not breathing or are not breathing adequately or normally by manually compressing a bag connected to an airway tube, face mask or other airway adjunct. One common form of a manual resuscitator is a bag valve mask (BVM) that is also sometimes referred to as an ambu bag. In a BVM, the airway tube is connected to a mask that is designed to fit over the face of a patient. In another type of manual resuscitator, the airway tube is connected to an endotracheal tube or advanced airway device that is used to intubate/ventilate the patient. Use of manual resuscitators to ventilate a patient is usually called "bagging" the patient and is necessary in medical emergencies when the patient's breathing is insufficient (respiratory failure) or has ceased completely (respiratory arrest). Use of the manual resuscitators force-feeds air or oxygen into the lungs in order to inflate them under pressure thus constituting a means to manually provide ventilation to a patient.

When using a manual resuscitator such as a BVM, bag compressions/ventilations performed improperly, such as at improper rates and/or durations, have been shown to cause detrimental effects including low survival rates in patients in cardiac arrest and life threatening complications such as gastric regurgitation and aspiration that can later lead to death. It is widely known from many clinical studies that very often ventilation rates are administered far in excess of the recommended and safe amounts established. This is very often done even by highly experienced well trained EMS personnel and personnel and can cause detrimental effects where life threatening conditions already exist in patients. Studies have found that even among highly trained and experienced medical personnel, the quality of manual and BVM ventilation is inconsistent and does not meet published guidelines. In one clinical observation study, it was found that ventilation rates during the field application of CPR (cardiopulmonary resuscitation) in a city with well-trained EMS personnel were observed to be far in excess of those recommended by the American Heart Association. This study found that professional rescuers responder and medical personnel consistently and inadvertently hyper-ventilated patients during actual resuscitations. This hyperventilation can lead to detrimental hemodynamic and survival consequences during low flow states such as when CPR is applied. The study concluded that unrecognized and inadvertent hyper-ventilation may be contributing to the currently dismal survival rates from cardiac arrest.

Manual resuscitators often are manufactured in different sizes to be used on patients of different age categories and are commonly available in adult, child, infant and neonate sizes. Particularly in the case of a small child, infant or neonate, over pressure ventilation could cause rupture of delicate lung tissue. Accordingly, in order to reduce this possibility, manual resuscitation apparatus typically includes a safety valve for venting air above a pre set pressure.

The prior art as also proposed equipping manual resuscitators with manometers or spirometers, and optionally $CO_2$ and/or CO sensors or pressure transducers for measuring expiratory flow, expiratory tidal volume, expiratory minute volume and ventilator frequency. See, for example, U.S. Pat. Nos. 5,722,394; 7,051,596; 7,172,557 and 7,357,033. However, without an apparatus and method to provide correct alerting/notifications of proper rates/timing of ventilations, proper consistent administration can be difficult, especially in the field under traumatic situations.

SUMMARY OF THE INVENTION

The present invention provides apparatus and method for use with ventilation devices such as bag valve masks to continually aid the user as to the proper rates/durations to ventilate patients in order to significantly reduce further harm and in turn provide proper crucial life saving ventilation. (References to a "patient," as the term is used herein, should be understood to also include training devices such as mannequins for training personnel to administer manual resuscitation/ventilation). As described below, a pacing apparatus is used to provide a user of a bag-type or other ventilation device an indication as to a proper rate, a proper duration of delivery or any combination of either at which ventilations/compressions should be initiated during each respiratory cycle. The pacing apparatus additionally may provide the proper duration for which the bag should be compressed once initiated. As the term is used herein, a bag compression duty-cycle should be taken to refer to either the rate at which the compressions are initiated or both the timing and duration of the bag compressions. (The term "compression" as used here refers to compressions of the bag that ventilates a patient (or training mannequin), to be distinguished from the chest compressions that are applied during CPR.) The indications of a specified compression duty-cycle may, for example, be in the form of a visual, tactile (such as vibrating or pulsating notification), or audio signal/indicator, or any combination thereof. For example, in the case where both the timing and duration are to be indicated, the apparatus may provide a signal that when present indicates to a user that the bag should be compressed and when absent indicates that the bag should be allowed to inflate. The pacing apparatus thus directly and continually alerts/notifies users of the proper rate or rate/durations for providing ventilation to patients and can help to prevent further harm and save lives.

In one embodiment a pacing apparatus for providing compression duty-cycle indications to a user of a manual resuscitator comprises a structure that contains the electronic circuitry configured to provide a visual, tactile, and/or audible indication of a specified compression duty-cycle for applying manual compressions to the bag of the manual resuscitator when ventilating a patient The electronic circuitry may be configured to accept a user input for defining one or more specified compression duty-cycles and the user input may be used for selecting between different specified compression duty-cycles. The electronic circuitry may be configured to accept the user input via a wireless communications link. The electronic circuitry may be configured with adult child, infant, and neonate and advanced airway settings for the compression duty-cycle. In the case where to signal provided to the user is a visual one, the electronic circuitry may be configured to illuminate the structure or lights mounted on the annular structure with a different color depending upon which setting for the compression duty-cycle is selected.

In one embodiment, the structure that houses the pacing apparatus electronic circuitry is a bracelet or other wearable item. The structure may: 1) provide visual compression duty-cycle indications to the user via one or more lights mounted on the bracelet or by illumination of the structure, 2) vibrate in order to provide indications of the compression duty-cycle, and/or 3) provide audible sounds to indicate the proper compression duty-cycle.

In one embodiment the structure housing the electronic circuitry is an annular structure adapted for interposition between a bag and an airway tube of a manual resuscitator, wherein the airway tube is connected to a face mask in the case where the manual resuscitator is a bag valve mask or is connected to an endotracheal (ET tube).

In various embodiments, the annular structure may be adapted to fit over an exit tube of the bag that connects to the airway tube or adapted to fit inline between fittings of the bag and the airway tube. As described above, the structure may provide visual, auditory, and/or tactile cues to the user to indicate when bag compressions should be applied. In one embodiment, the electronic circuitry may be configured to illuminate the annular structure in accordance with the specified compression duty-cycle to provide a visual indication from any viewing angle. In another embodiment, the electronic circuitry may be configured to transmit indications of the phases of the specified compression duty cycle to a peripheral device such as a bracelet or other wearable item that is configured to provide audible, vibratory, and/or visual indications of the compression duty-cycle to a user.

BRIEF DESCRIPTION OF THE DRAWINGS

Further features and advantages of the present invention will be seen from the following detailed description, taken in conjunction with the accompanying drawings, wherein like numerals depict like parts, and wherein FIGS. 1a-1c, illustrate respectively, a side perspective view, a top view and a bottom view of a manual resuscitator and pacing apparatus in accordance with the present invention;

FIG. 2 is a view similar to 1a, showing a pacing apparatus in accordance with the present invention, installed on a bag valve mask;

FIGS. 3a and 3b are views, similar to FIG. 2 showing alternative installations of a pacing apparatus in accordance with the present invention;

FIGS. 4a-4d illustrate other forms of pacing apparatus in accordance with the present invention.

DETAILED DESCRIPTION OF THE INVENTION

Figure 5:
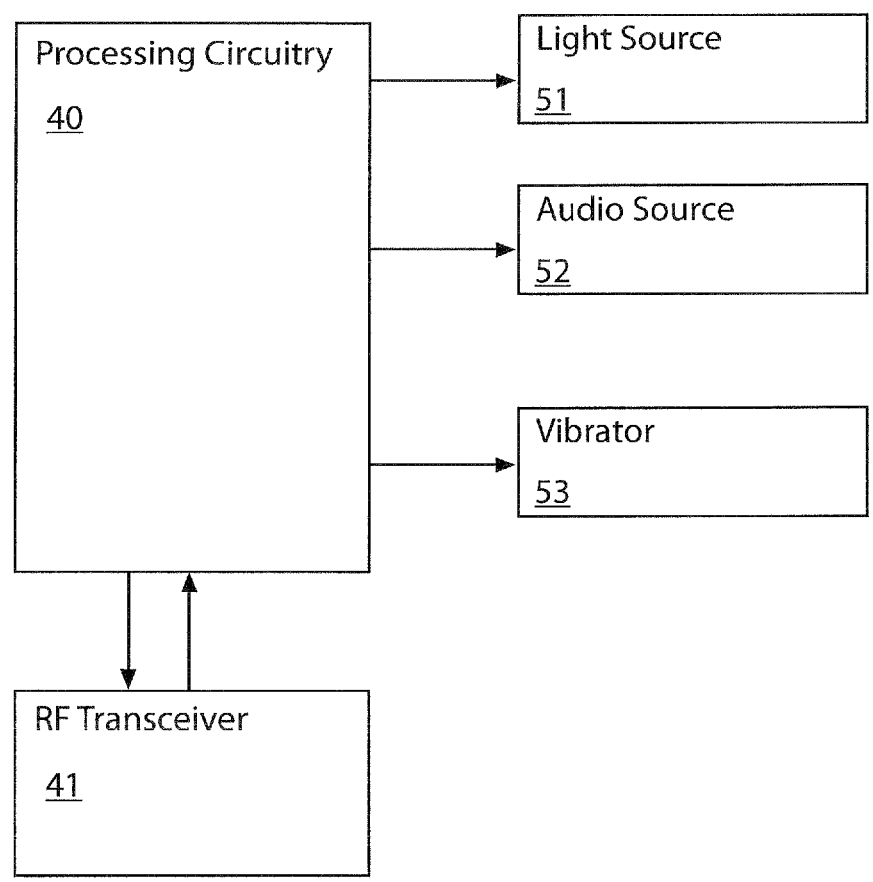
FIG. 5 is a block diagram of an embodiment of the present invention.

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in limiting sense. The scope of the present subject matter is defined by the appended claims, along with the full scope of legal equivalents to which such claims are entitled.

FIGS. 1a and 1b illustrate the apparatus according to one embodiment of the invention. The apparatus includes a self-contained pacing apparatus generally indicated at 10 which is installed inline and integrated between the bag 12 and face mask 14. The pacing apparatus 10 includes an on/off switch 16, a selection switch 18 and a plurality of lights 20, 22, 24, and 26 for providing compression duty-cycle indication to the user. Alternatively, on/off switch 16 and selection switch 18 may be combined into a single switch. Preferably, each light is a different color to indicate which setting is being used, e.g. adult, child, infant or neonate. Alternatively, all of the lights can be the same color with one light being lit indicating a duty-cycle for a neonate, two lights a duty-cycle for infants, three lights for a duty-cycle for children, and four lights a duty-cycle for adults. The lights may be light emitting diodes (LEDs) or other light sources that are operated by electronic circuitry housed within the pacing apparatus. The pacing apparatus also may include a sound-emitting device 28 for providing audible indication of a specified compression duty-cycle to the user.

Alternatively, on/off switch 16 and selection switch 18 may be combined into a single switch. Also, as shown in FIG. 1c, the on/off switch may be operated by twisting the pacing apparatus structure 10.

FIG. 2 shows the pacing apparatus 10 as being interposed between the exit tube of the bag 12 and the airway tube 30 that in turn is connected to an advanced airway mask or an ET tube 31. In one embodiment visual indications of the desired compression duty-cycle are provided by the electronic circuitry operating a light source to illuminate the pacing apparatus, where the pacing apparatus is at least partially made of translucent material. In this way, the illumination may be observed from a number of different viewing angles or from any viewing angle.

FIGS. 3a and 3b show alternative embodiments for interposing the pacing apparatus between the exit tube of the bag 12 and the airway tube 30. In one embodiment the pacing apparatus is adapted to fit over the exit tube of the bag 12 that connects to the airway tube 30. In another embodiment, the pacing apparatus is adapted to fit inline between fittings 32, 34 of the bag 12 and the airway tube or mask.

FIGS. 4a-4d illustrates an embodiment of a pacing apparatus in the form of a wristband 4a, 4b, 4c or clip 4d.

In the case of the apparatus shown in FIG. 4a, the pacing apparatus may include a light or series of lights 42.

In the case of the apparatus shown in FIG. 4b, the apparatus 44 may comprise a sound emitter 46.

In the case of the pacing apparatus shown in FIG. 4c, the pacing apparatus may include a vibrator 48.

Alternatively as shown in FIG. 4d, the pacing apparatus may take the form of a clip or pendant 50 designed to attach to a belt loop or worn like a pendant.

FIG. 5 illustrates the components of the electronic circuitry according to one embodiment which are housed within the annular structure. Processing circuitry 40 stores different compression duty-cycle settings and actuates one or more indicators for providing the duty-cycle indication to a user. The device may be equipped with any or all of a light source 51, audio source 52, or a vibrator 53 for this purpose. A user input (e.g., buttons or switches on the structure) may be interfaced to the processing circuitry to allow the user to turn the apparatus on or off, program different settings for the compression duty-cycle, and/or select between different pre-programmed settings. A radio-frequency (RF) transceiver 41 also may interfaced to the processing circuitry to provide a wireless communications channel. In various embodiments, the wireless communications channel may be used to accept different settings for the compression duty-cycle or to output indications of the duty-cycle during operation to one or more peripheral devices. Also housed within the annular structure is a battery (not shown) for providing power to the electronic circuitry.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

The subject matter has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:

1. A manual ventilation device, comprising:
   a ventilation bag;
   a face mask; and
   a self-contained pacing apparatus integrated between the ventilation bag and the face mask, wherein the pacing apparatus comprises:
   an annular structure containing electronic circuitry configured with a plurality of user selectable pre-programmed compression/ventilation duty-cycles;
   user input buttons positioned on the annular structure, wherein one of the plurality of user selectable pre-programmed compression/ventilation duty-cycles is selectable by a user by activation of the user input buttons;
   a duty cycle selection indicator positioned on the annular structure and interfaced with the electronic circuitry, wherein the duty cycle selection indicator is configured to provide an indication of a selection of one of the plurality of user selectable pre-programmed compression/ventilation duty-cycles to the user, wherein the indication is at least one of: a visual indicator, a tactile indicator, and an audible indicator; and
   wherein the annular structure is at least partially made of a translucent material so that the visual indicator can be observed from a number of different viewing angles, and
   wherein the pacing apparatus is self-contained, and the electronic circuitry is housed entirely within the pacing apparatus.

2. The apparatus of claim 1, wherein the annular structure is adapted to fit over an annular exit tube of the bag for connection to an airway tube.

3. The apparatus of claim 1, wherein the annular structure is adapted to fit inline between annular fittings of the bag and an airway tube.

4. The apparatus of claim 1, wherein the electronic circuitry is configured to accept a user input for defining one or more specified compression/ventilation duty-cycles.

5. The apparatus of claim 1, wherein the electronic circuitry is configured to accept a user input for selecting between different specified compression/ventilation duty-cycles.

6. The apparatus of claim 1, wherein the electronic circuitry is configured with adult, child, infant, and neonate compression/ventilation duty-cycle settings.

7. The apparatus of claim 1, wherein the electronic circuitry is configured to provide a signal to illuminate the annular structure with a different color depending upon which compression/ventilation duty-cycle is selected.

8. The apparatus of claim 1, wherein the electronic circuitry also is configured to transmit indications of phases of a compression/ventilation duty-cycle to a peripheral device that is configured to provide audible, vibratory, and/or visual indications of the compression/ventilation duty-cycle to a user.

9. The apparatus of claim 1, wherein the electronic circuitry is configured to provide a signal to illuminate a different number of lights depending on which compression/ventilation duty-cycle is selected.

10. The apparatus of claim 1, wherein the electronic circuitry is configured to provide a signal to a visual and a tactile and/or audible indicator.

11. The apparatus of claim 1, wherein the user selectable pre-set compression/ventilation duty-cycles are selected from the group consisting of an adult, a child, an infant and a neonate.

12. A manual ventilation device, comprising:
    a ventilation bag;
    a face mask; and
    a self-contained pacing apparatus integrated inline between the ventilation bag and the face mask, wherein the pacing apparatus comprises:
    an annular housing;
    electronic circuitry entirely contained within the annular housing;
    at least one user input structure including user input buttons positioned on the annular housing and interfaced with the electronic circuitry, wherein at least one of a plurality of pre-programmed compression/ventilation duty-cycles is selected upon user manipulation of the user input buttons;
    a plurality of light sources included with the annular housing and interfaced with the electronic circuitry, wherein at least one of the plurality of light sources indicates a selection by a user of one of the plurality of pre-programmed compression/ventilation duty-cycles; and
    a proper ventilation indicator included with the annular housing and interfaced with the electronic circuitry, wherein the proper ventilation indicator indicates at least one of: a proper ventilation rate and a proper ventilation duration for delivery of a breathing gas to a patient.

13. The pacing apparatus for use with a manual ventilation device of claim 12, further comprising an activation switch carried by the annular housing, wherein the activation switch is activated by twisting the annular housing.

14. The pacing apparatus for use with a manual ventilation device of claim 12, wherein the proper ventilation indicator further comprises: a visual indicator, a tactile indicator, and an audible indicator.

15. The pacing apparatus for use with a manual ventilation device of claim 12, wherein the at least one of the plurality of pre-programmed compression/ventilation duty-cycles is selected based solely upon user manipulation of the input structure.

16. A manual ventilation kit, comprising:
a ventilation bag;
a face mask; and
a self-contained pacing apparatus for use with the ventilation bag and the face mask, wherein the pacing apparatus comprises:
an annular structure containing electronic circuitry configured with a plurality of user selectable pre-programmed compression/ventilation duty-cycles;
user input buttons positioned on the annular structure, wherein one of the plurality of user selectable pre-programmed compression/ventilation duty-cycles is selectable by a user by activation of the user input buttons;
a duty cycle selection indicator positioned on the annular structure and interfaced with the electronic circuitry, wherein the duty cycle selection indicator is configured to provide an indication of a selection of one of the plurality of user selectable pre-programmed compression/ventilation duty-cycles to the user, wherein the indication is at least one of: a visual indicator, a tactile indicator, and an audible indicator; and
wherein the annular structure is at least partially made of a translucent material so that the visual indicator can be observed from a number of different viewing angles, and
wherein the pacing apparatus is self-contained, and the electronic circuitry is housed entirely within the pacing apparatus.

17. The kit of claim 16, wherein the electronic circuitry is configured to accept a user input for defining one or more specified compression/ventilation duty-cycles, and/or for selecting between different specified compression/ventilation duty-cycles.

18. The kit of claim 16, wherein the electronic circuitry is configured with adult, child, infant, and neonate compression/ventilation duty-cycle settings.

19. The apparatus of claim 8, wherein the peripheral device comprises a wristband configured to provide audible, vibratory, and/or visual indications of the compression/ventilation duty-cycle to a user.

* * * * *